US00PP33686P2

(12) United States Plant Patent
Barends

(10) Patent No.: US PP33,686 P2
(45) Date of Patent: Nov. 23, 2021

(54) ***OSTEOSPERMUM* PLANT NAMED 'DOOSTMARYEL 21'**

(50) Latin Name: *Osteospermum ecklonis*
Varietal Denomination: Doostmaryel 21

(71) Applicant: DUMMEN GROUP B.V., De Lier (NL)

(72) Inventor: Eveline Barends, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/242,217

(22) Filed: Apr. 27, 2021

(51) Int. Cl.
*A01H 6/14* (2018.01)
*A01H 5/02* (2018.01)

(52) U.S. Cl.
USPC ..... Plt./360

(58) Field of Classification Search
USPC ..... Plt./360
See application file for complete search history.

(56) References Cited

PUBLICATIONS

PLUTO Plant Variety Database Jun. 24, 2021. p. 1.*

* cited by examiner

*Primary Examiner* — Annette H Para
(74) *Attorney, Agent, or Firm* — C. Anne Whealy

(57) ABSTRACT

A new and distinct cultivar of *Osteospermum* plant named 'Doostmaryel 21', characterized by its compact, uniform and mounding plant habit; moderately vigorous growth habit; freely and uniformly branching habit; freely and early flowering habit; large single-type inflorescences with bright yellow-colored ray florets; and good garden performance.

1 Drawing Sheet

Botanical designation: *Osteospermum ecklonis.*
Cultivar denomination: 'DOOSTMARYEL 21'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Nov. 12, 2020, application number 2020/2855. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Osteospermum* plant, botanically known as *Osteospermum ecklonis*, and hereinafter referred to by the name 'Doostmaryel 21'.

The new *Osteospermum* plant is a product of a planned breeding program conducted by the Inventor in Puerto Lumbreras, Spain and De Lier, The Netherlands. The objective of the program is to create and develop new vigorous *Osteospermum* plants that are freely and uniformly branching with numerous large inflorescences with unique and attractive ray and disc floret coloration.

The new *Osteospermum* plant originated from a cross-pollination by the Inventor during the winter of 2013 of *Osteospermum ecklonis* 'Margarita Plus Yellow', not patented, as the female, or seed, parent with a proprietary selection of *Osteospermum ecklonis* identified as code number QQ11-000059-005, not patented, as the female, or seed, parent. The new *Osteospermum* plant was discovered and selected by the Inventor as a single flowering plant within the progeny of the stated cross-pollination in a controlled greenhouse environment in De Lier, The Netherlands in July, 2014.

Asexual reproduction of the new *Osteospermum* plant by terminal vegetative cuttings in a controlled greenhouse environment in De Lier, The Netherlands since August, 2014 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Doostmaryel 21'. These characteristics in combination distinguish 'Doostmaryel 21' as a new and distinct *Osteospermum* plant:

1. Compact, uniform and mounding plant habit.
2. Moderately vigorous growth habit.

3. Freely and uniformly branching habit.
4. Freely and early flowering habit.
5. Large single-type inflorescences with bright yellow-colored ray florets.
6. Good garden performance.

Plants of the new *Osteospermum* differ primarily from plants of the female parent, 'Margarita Plus Yellow', in ray floret color as ray florets of plants of the new *Osteospermum* are darker yellow in color than ray florets of plants of 'Margarita Plus Yellow'.

Plants of the new *Osteospermum* differ primarily from plants of the male parent selection in growth habit as plants of the new *Osteospermum* are more compact than and not as vigorous as plants of the male parent selection.

Plants of the new *Osteospermum* can be compared to plants of the *Osteospermum ecklonis* 'Fidostyel', disclosed in U.S. Plant Pat. No. 21,342. In side-by-side comparisons, plants of the new *Osteospermum* differ primarily from plants of 'Fidostyel' in the following characteristics:

1. Plants of the new *Osteospermum* are more freely branching than plants of 'Fidostyel'.
2. Plants of the new *Osteospermum* are more freely flowering than plants of 'Fidostyel'.
3. Plants of the new *Osteospermum* have larger inflorescences with fewer ray florets than plants of 'Fidostyel'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant. The photograph is a side perspective view of a typical flowering plant of 'Doostmaryel 21' grown in a container.

DETAILED BOTANICAL DESCRIPTION

The aforementioned photograph, following observations and measurements describe plants grown during the summer autumn in 12-cm containers in a glass-covered greenhouse in De Lier, The Netherlands and under cultural practices typical of commercial *Osteospermum* production. During the production of the plants, day temperatures ranged from 16° C. to 18° C., night temperatures ranged from 12° C. to 14° C. and light levels averaged 135 watt/m$^2$. Plants were pinched five weeks after sticking unrooted cuttings and plants were 13 weeks old when the photograph was taken and 18 weeks old when the description was taken. In the following description, color references are made to The Royal Horticultural Society Colour Chart, Fifth Edition, except where general terms of ordinary dictionary significance are used.

Botanical classification: *Osteospermum ecklonis* 'Doostmaryel 21'.

Parentage:

*Female, or seed, parent.*—*Osteospermum ecklonis* 'Margarita Plus Yellow', not patented.

*Male, or pollen, parent.*—Proprietary selection of *Osteospermum ecklonis* identified as code number QQ11-000059-005, not patented.

Propagation:

*Type.*—Terminal vegetative cuttings.

*Time to initiate roots, summer.*—About 18 days at temperatures about 22° C. to 30° C.

*Time to initiate roots, winter.*—About 21 days at temperatures about 22° C. to 30° C.

*Time to produce a rooted cutting, summer.*—About 25 days at temperatures about 22° C. to 30° C.

*Time to produce a rooted cutting, winter.*—About 28 days at temperatures about 20° C. to 25° C.

*Root description.*—Medium in thickness, fibrous; typically whitish grey in color, actual color of the roots is dependent on substrate composition, water quality, fertilizers, substrate temperature and age of roots.

*Rooting habit.*—Moderately freely branching; medium density.

Plant description:

*Plant form and growth habit.*—Compact, uniform and mounding plant habit; relatively short internodes, dense and bushy growth habit; moderately vigorous growth habit and moderate growth rate.

*Plant height, soil level to top of foliar plane.*—About 17 cm.

*Plant height, soil level to top of floral plane.*—About 21 cm.

*Plant diameter.*—About 25 cm.

*Lateral branches.*—Quantity per plant: Freely branching habit, about six primary lateral branches each with about three to four secondary lateral branches developing per plant; pinching enhances lateral branch development. Length: About 17 cm. Diameter: About 3 mm. Internode length: About 7 mm. Strength: Strong, sturdy. Texture and luster: Smooth, glabrous; semi-glossy. Color, developing and developed: Close to 144B.

*Leaf description.*—Arrangement: Alternate, simple; sessile. Length: About 5.3 cm. Width: About 1.5 cm. Shape: Spatulate. Apex: Acute. Base: Attenuate. Margin: Serrate and lobe with medium depth and divergent sinuses. Texture and luster, upper surface: Pubescent; leathery; slightly glossy. Texture and luster, lower surface: Smooth, glabrous; leathery; slightly dull. Venation pattern: Pinnate. Color: Developing leaves, upper surface: Close to N137D. Developing leaves, lower surface: Close to 138A. Fully expanded leaves, upper surface: Close to N137D; venation, close to 138A. Fully expanded leaves, lower surface: Close to 144B; venation, close to 144B.

Inflorescence description:

*Appearance and aspect.*—Terminal and axillary inflorescences; inflorescences positioned beyond the foliar plane on strong peduncles and face mostly upright to outwardly; single-type inflorescence form with lanceolate-shaped ray florets and tubular disc florets; ray and disc florets developing acropetally on a capitulum.

*Flowering habit.*—Freely flowering habit; about nine to eleven open inflorescences per plant.

*Fragrance.*—None detected.

*Flowering response.*—In The Netherlands, plants of the new *Osteospermum* flower continuously from spring until first frost in the autumn; early flowering habit, plants begin flowering about 70 to 91 days after sticking cuttings.

*Inflorescence longevity.*—Inflorescences last about one week on the plant; inflorescences not persistent.

*Inflorescence buds*.—Height: About 1.5 cm. Diameter: About 9 mm. Shape: Ovoid. Texture and luster: Smooth, glabrous; semi-glossy. Color: Close to 137B.

*Inflorescence size*.—Diameter: About 9 cm. Depth (height): About 1 cm. Disc diameter: About 1 cm. Receptacle diameter: About 8 mm. Receptacle height: About 7 mm. Receptacle color: Close to 137C.

*Ray florets*.—Quantity per inflorescence and arrangement: About 21 arranged in one to two whorls. Length: About 4 cm. Width: About 1 cm. Shape: Lanceolate. Apex: Emarginate. Base: Obtuse. Margin: Entire. Aspect: Mostly flat. Texture and luster, upper and lower surfaces: Smooth, glabrous; matte. Color: When opening, upper surface: Close to 12A. When opening, lower surface: Close to 9A; venation, close to 179C. Fully opened, upper surface: Close to 10A; venation, close to 10A; color does not change with subsequent development. Fully opened, lower surface: Close to 9B; venation, close to 179C; color becoming closer to 12A with subsequent development.

*Disc florets*.—Quantity per inflorescence and arrangement: About 56 arranged in about five whorls. Length: About 6 mm. Diameter: About 1 mm. Shape: Tubular with five pointed apices. Apex: Dentate. Aspect: Upright. Texture and luster: Smooth, glabrous; matte. Color: When developing and fully developed, inner surface: Close to 7A; color becoming closer to 14A with subsequent development. When developing and fully developed, outer surface: Close to 8D; color does not change with subsequent development.

*Phyllaries*.—Quantity per inflorescence and arrangement: About 21 arranged in a single whorl. Length: About 8 mm. Width: About 1 mm. Shape: Lanceolate. Apex: Acute. Base: Cuneate. Margin: Entire. Texture and luster, upper and lower surfaces: Smooth, glabrous; matte. Color, upper surface: Close to 138A. Color, lower surface: Close to 139C.

*Peduncles*.—Length: About 6 cm. Diameter: About 2 mm. Strength: Strong. Aspect: Mostly upright to outwardly slanting. Texture and luster: Smooth, glabrous; semi-glossy. Color: Close to 144A.

*Reproductive organs*.—Androecium: Present on disc florets only. Filament length: About 2 mm. Filament color: Close to 200A. Anther size: About 1 mm by 2 mm. Anther shape: Oval. Anther color: Close to 200A. Pollen amount: Abundant. Pollen color: Close to 23A. Gynoecium: Present on both ray and disc florets. Pistil length: About 5 mm. Stigma shape: Tri-parted. Stigma diameter: About 0.2 mm. Stigma color: Close to 200A. Style length: About 2 mm. Style color: Close to 200A. Ovary color: Close to 144D.

*Fruits/seeds*.—To date, fruit and seed development has not been observed on plants of the new *Osteospermum*.

Pathogen & pest resistance: Plants of the new *Osteospermum* have not been observed to be resistant to pathogens and pests common to *Osteospermum* plants.

Garden performance: Plants of the new *Osteospermum* have been observed to have good garden performance and to tolerate rain, wind and temperatures ranging from about 5° C. to about 35° C.

It is claimed:

1. A new and distinct *Osteospermum* plant named 'Doostmaryel 21' as illustrated and described.

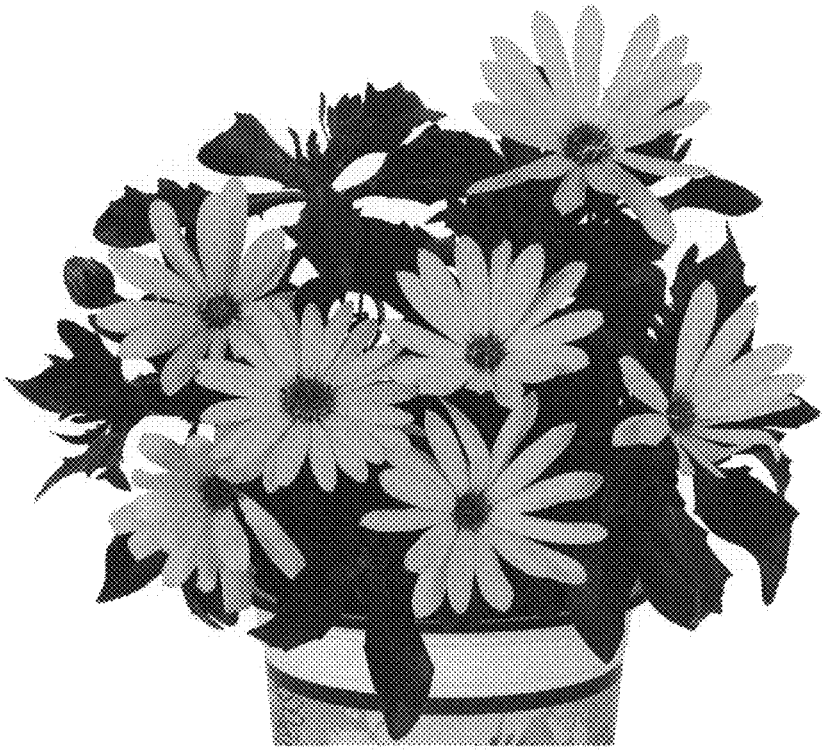

* * * * *